United States Patent [19]

Neuzil et al.

[11] 4,358,322
[45] Nov. 9, 1982

[54] PROCESS FOR SEPARATING A KETOSE FROM AN ALDOSE BY SELECTIVE ADSORPTION

[75] Inventors: Richard W. Neuzil, Downers Grove; James W. Priegnitz, Elgin, both of Ill.

[73] Assignee: UOP Inc., Des Plaines, Ill.

[21] Appl. No.: 74,856

[22] Filed: Sep. 13, 1979

Related U.S. Application Data

[62] Division of Ser. No. 690,768, May 27, 1976, Pat. No. 4,226,977.

[51] Int. Cl.$^3$ .......................... C13K 1/00; C13K 3/00; C13K 11/00
[52] U.S. Cl. ...................................... 127/46.2; 127/9; 127/46.1; 127/46.3; 210/264; 210/424; 210/676; 536/1.1
[58] Field of Search .................... 127/46.2, 46.3, 46.1

[56] References Cited

U.S. PATENT DOCUMENTS

| | | | |
|---|---|---|---|
| 2,985,589 | 5/1961 | Broughton | 210/264 X |
| 3,706,812 | 12/1972 | Derosset | 260/674 SA |
| 3,761,533 | 9/1973 | Otani | 264/674 SA |
| 4,014,711 | 3/1977 | Odawara | 127/46.3 |
| 4,157,267 | 6/1979 | Odawara | 127/46.2 |
| 4,226,639 | 10/1980 | Michalko | 127/46.3 X |
| 4,238,243 | 12/1980 | Tu | 127/46.3 |
| 4,248,737 | 2/1981 | Kulprathipanja | 127/46.3 X |
| 4,287,001 | 9/1981 | Kulprathipanja | 127/46.3 X |

*Primary Examiner*—Sidney Marantz
*Attorney, Agent, or Firm*—James R. Hoatson, Jr.; Louis A. Morris; William H. Page, II

[57] ABSTRACT

A process for separating a ketose from a feed mixture comprising a ketose and an aldose which process comprises contacting the mixture with an adsorbent comprising a X zeolite containing one or more selected cations at exchangeable cationic sites thereby selectively adsorbing a ketose from the feed mixture and thereafter recovering the ketose. Preferably, the ketose will be recovered by desorption from the adsorbent with a desorbent material.

3 Claims, No Drawings

PROCESS FOR SEPARATING A KETOSE FROM AN ALDOSE BY SELECTIVE ADSORPTION

CROSS-REFERENCE TO RELATED APPLICATIONS

This application is a division of our prior, copending application Ser. No. 690,768 filed May 27, 1976, U.S. Pat. No. 4,226,977, which application is incorporated herein by reference thereto.

BACKGROUND OF THE INVENTION

1. Field of the Invention

The field of art to which this invention pertains is the solid-bed adsorptive separation of monosaccharides. More specifically, the invention relates to a process for separating a ketose from a mixture comprising a ketose and an aldose which process employs an adsorbent comprising a crystalline aluminosilicate which selectively adsorbs a ketose from the feed mixture.

2. Description of the Prior Art

It is well known in the separation art that certain crystalline aluminosilicates can be used to separate hydrocarbon types from mixtures thereof. As a few examples, a separation process disclosed in U.S. Pat. Nos. 2,985,589 and 3,201,491 uses a type A zeolite to separate normal paraffins from branched-chain paraffins and processes described in U.S. Pat. Nos. 3,265,750 and 3,510,423 use type X or type Y zeolites to separate olefinic hydrocarbons from paraffinic hydrocarbons. In addition to their use in processes for separating hydrocarbon types, X and Y zeolites have been employed in processes to separate individual hydrocarbon isomers. As a few examples, adsorbents comprising X and Z zeolites are used in the process described in U.S. Pat. No. 3,114,782 to separate alkyl-trisubstituted benzene isomers; in the process described in U.S. Pat. No. 3,864,416 to separate alkyl-tetrasubstituted monocyclic aromatic isomers; in the process described in U.S. Pat. No. 3,668,267 to separate specific alkyl-substituted naphthalenes. Because of the commercial importance of paraxylene, perhaps the more well-known and extensively used hydrocarbon isomer separation processes are those for separating para-xylene from a mixture of $C_8$ aromatics. In processes described in U.S. Pat. Nos. 3,558,730; 3,558,732; 3,626,020; 3,663,638; and 3,734,974 for example adsorbents comprising particular zeolites are used to separate paraxylene from feed mixtures comprising para-xylene and at least one other xylene isomer by selectively adsorbing para-xylene over the other xylene isomers.

In contrast, our invention relates to the separation of nonhydrocarbons and more specifically to the separation of monosaccharides. We have discovered that adsorbents comprising certain zeolites containing one or more selected cations at the exchangeable cationic sites exhibit adsorptive selectivity for a ketose with respect to an aldose thereby making separation of a ketose from a mixture comprising a ketose and an aldose by solid-bed selective adsorption possible. In a specific embodiment our process is a process for separating fructose from a mixture comprising fructose and glucose.

Fructose is considered to be the most soluble and the sweetest of the sugars. Relative to sucrose having a sweetness of 1.0, fructose has a relative sweetness of about 1.4 while that of glucose is 0.7. The literature indicates that one of its uses in pure form is as a source of calories for patients who must be fed intervenously and that under conditions of stress such as surgery, starvation, and diabetes fructose administered intravenously is utilized normally whereas glucose is not. Other indicated advantages of fructose over glucose for intervenous feeding are a more adequate provision of calories as a result of less loss of sugar in the urine and a shorter infusion time (with consequently less discomfort to the patient), and a more rapid formation of liver glycogen. While fructose exists widely in nature the methods for isolating high-purity fructose are, however, more difficult than the primary method for obtaining high-purity glucose. High-purity glucose is readily manufactured from starch (which is made up exclusively of glucose units) by hydrolysis with mineral acids at elevated temperature followed by refining and crystallization of the hydrolyzate while one method of obtaining high-purity fructose on the other hand involves hydrolysis of sucrose, separation of fructose as an insoluble lime-fructose complex, liberation of fructose by acidification of the complex with acids that form insoluble calcium salts (such as carbonic or phosphoric acid), removal of cation and anion contaminants by means of cation- and anion-exchange resins, concentration of the resulting solution to a thick syrup in vacuo, and finally crystallization of fructose. Extensive studies have been made on the production of fructose by hydrolysis of fructose-bearing polysaccharides extracted from the Jerusalem artichoke. The Jerusalem artichoke is not a crop plant in the United States, however, and additionally the harvesting of the artichoke tubers (where the polysaccharides are stored) is a relatively costly and seasonal operation. Several methods of separating glucose from invert sugar, leaving fructose, have also been attempted, such as formation of insoluble benzidine derivatives of glucose and sodium chloride addition compounds of glucose, but these have not been practicable. Because of the difficulty in separating or concentrating fructose, solutions of fructose in combination with one or more other sugars are used to obtain the benefit of the higher sweetness of the fructose. Invert sugar solutions, which contain fructose and glucose, and "high fructose" corn syrup, which contains typically 40–45% fructose and 50–55% glucose as the principal sugars, are examples. Our invention offers an easier more direct process for separating fructose from a feed mixture containing fructose and glucose to obtain a product stream enriched in fructose and a product stream enriched in glucose. Both products can be used in confectionery and bakery products, in the canning of fruits and vegetables, in beverages and in other products requiring such sweeteners.

SUMMARY OF THE INVENTION

It is accordingly a broad objective of our invention to provide a process for separating a ketose from a feed mixture containing a ketose and an aldose to produce a ketose product stream and an aldose product stream containing higher concentrations of a ketose and an aldose respectively than were contained in the feed mixture. More specifically it is an objective of our invention to provide a process for separating fructose from a feed mixture, such as an invert sugar solution or a high fructose corn syrup, containing fructose and glucose.

In brief summary our invention is, in one embodiment, a process for separating a ketose from a feed mixture comprising a ketose and an aldose which process comprises contacting at adsorption conditions the mixture with an adsorbent comprising a X zeolite containing at exchangeable cationic sites a cation selected from the group consisting of sodium, barium and strontium thereby selectively adsorbing the ketose and thereafter recovering the ketose.

In another embodiment our invention is a process for separating a ketose from a mixture comprising a ketose and an aldose which process comprises contacting at adsorption conditions the mixture with an adsorbent comprising a X zeolite containing at exchangeable cationic sites a cation pair selected from the group consisting of barium and potassium and barium and strontium thereby selectively adsorbing the ketose and thereafter recovering the ketose.

Other objectives and embodiments of our invention encompass details about feed mixtures, adsorbents, desorbent materials and operating conditions all of which are hereinafter disclosed in the following discussion of each of the facets of the present invention.

DESCRIPTION OF THE INVENTION

At the outset the definitions of various terms used throughout the specification will be useful in making clear the operation, objects and advantages of our process.

A feed mixture is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, a ketose is an extract component and an aldose is a raffinate component. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity ketose product or aldose product (or both) at high recoveries, it will be appreciated that an extract component is never completely adsorbed by the adsorbent, nor is a raffinate component completely non-adsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of a ketose to that of a less selectively adsorbed aldose will be lowest in the raffinate stream, next highest in the feed mixture, and the highest in the extract stream. Likewise, the ratio of the concentration of a less selectively adsorbed aldose to that of the more selectively adsorbed ketose will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process its non-selective void volume together with its selective pore volume carries fluid into that zone. The non-selective void volume is utilized in determining the amount of fluid which should pass into the same zone in a counter-current direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed mixtures which can be charged to the process of our invention will be those comprising a ketose and an aldose and more specifically and preferably will be aqueous solutions of a ketose an an aldose. While the feed mixture may contain more than one ketose and more than one aldose, typically the feed mixture will contain one ketose and one aldose each in concentrations of from about 0.5 wt. % to about 30 wt. % and more preferably from about 1 to about 15 wt. %. The process may be used to separate a ketopentose from an aldopentose but more typically will be used to separate a ketohexose from an aldohexose. Well known ketohexoses are fructose (levulose) and sorbose; well known aldohexoses are glucose (dextrose), mannose and galactose while lesser-known aldohexoses are gulose, talose, allose, altrose, and idose. Preferred feed mixtures containing hexoses will be aqueous solutions of invert sugar formed when sucrose is hydrolyzed by acidic materials into equi-molar amounts of fructose and glucose. Other preferred feed mixtures will be aqueous solutions of high fructose (typically about 40–45%) corn syrup produced by the enzymatic isomerization of glucose solutions.

Desorbent materials used in various prior art adsorptive separation processes vary depending upon such factors as the type of operation employed. In the swing-bed system in which the selectively adsorbed feed component is removed from the adsorbent by a purge stream desorbent selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated at substantially constant pressures and temperatures to insure liquid phase, the desorbent material relied upon must be judiciously selected to satisfy, hopefully, all of several criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material the purity of the extract product and the raffinate product would not be very high, nor would the desorbent material be available for reuse in the process. It is contemplated that at least a portion of the desorbent material will be separated from the extract and the raffinate streams by distillation but other separation methods such as reverse osmosis may also be employed alone or in combination with distillation. Since the raffinate and extract products are foodstuffs intended for human consumption, desorbent materials should also be non-toxic. Finally, desorbent materials should also be materials which are preferably readily available and therefore reasonable in cost. We have found that water satisfies these criteria and is a suitable desorbent material for our process.

The prior art has also recognized that certain characteristics of adsorbents are highly desirable, if not absolutely necessary, to the successful operation of a selective adsorption process. Such characteristics are equally important to this process. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown as Equation 1 below.

Equation 1
$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or less than 1 with respect to all extract components so that all of the extract components can be extracted as a class and all raffinate components cleanly rejected into the raffinate stream. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular ketose or aldose or both all diluted in desorbent is injected for a duration of several minutes. Desorbent flow is resumed, and the tracer and the ketose and aldose are eluted as in a liquid-solid chromatographic operation. The effluent can be analyzed on-stream or alternatively effluent samples can be collected periodically and later analyzed separately by analytical equipment and traces of the envelopes of corresponding component peaks developed.

From information derived from the test adsorbent performance can be rated in terms of void volume, capacity index for an extract component, selectivity for one component with respect to the other, and the rate of desorption of an extract component by the desorbent. The capacity index of an extract component may be characterized by the distance between the center of the peak envelope of the extract component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquidsolid contacting device. The general operating principles of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, Calif., Mar. 28 through Apr. 2, 1971.

Adsorbents to be used in the process of this invention will comprise specific crystalline aluminosilicates or molecular sieves. Particular crystalline aluminosilicates encompassed by the present invention include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" particularly when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the separation of a ketose from an aldose is apparently dependent on differences in electrochemical attraction of a ketose and the adsorbent and an aldose and the adsorbent rather than on physical size differences in the molecules.

In hydrated form, the crystalline aluminosilicates generally encompass those zeolites represented by the Formula 1 below:

Formula 1

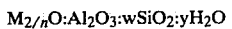

where "M" is a cation which balances the electrovalence of the aluminum-centered tetrahedra and which is generally referred to as an exchangeable cationic site, "n" represents the valence of the cation, "w" represents the moles of SiO$_2$, and "y" represents the moles of water. The generalized cation "M" may be monovalent, divalent or trivalent or mixtures thereof.

The prior art has generally recognized that adsorbents comprising X and Y zeolites can be used in certain adsorptive separation processes. These zeolites are described and defined in U.S. Pat. Nos. 2,882,244 and 3,120,007 respectively incorporated herein by reference thereto. The X zeolite in the hydrated or partially hydrated form can be represented in terms of mole oxides as shown in Formula 2 below:

Formula 2

$(0.9\pm0.2)M_{2/n}O:Al_2O_3:(2.5\pm0.5)SiO_2:yH_2O$ where "M" represents at least one cation having a valence of not more than 3, "n" represents the valence of "M", and "y" is a value up to about 9 depending upon the identity of "M" and the degree of hydration of the crystal. As noted from Formula 2 the SiO$_2$/Al$_2$O$_3$ mole ratio of X zeolite is 2.5±0.5. The cation "M" may be one or more of a number of cations such as a hydrogen cation, an alkali metal cation, or an alkaline earth cation, or other selected cations, and is generally referred to as an exchangeable cationic site. As the X zeolite is initially prepared, the cation "M" is usually predominately sodium and the zeolite is therefore referred to as a sodium-X zeolite. Depending upon the purity of the reactants used to make the zeolite, other cations mentioned above may be present, however, as impurities. The Y zeolite in the hydrated or partially hydrated form can be similarly represented in terms of mole oxides as in Formula 3 below.

Formula 3

$(0.9\pm0.2)M_{2/n}O:Al_2O_3:wSiO_2:yH_2O$ where "M" is at least one cation having a valence not more than 3, "n" represents the valence of "M", "w" is a value greater than about 3 up to 8, and "y" is a value up to about 9 depending upon the identity of "M" and the degree of hydration of the crystal. The SiO$_2$/Al$_2$O$_3$ mole ratio for Y zeolites can thus be from about 3 to about 6. Like the X zeolite, the cation "M" may be one or more of a variety of cations but, as the Y zeolite is initially prepared, the cation "M" is also usually predominately sodium. A Y zeolite containing predominately sodium cations at the exchangeable cationic sites is therefore referred to as a sodium-Y zeolite.

Cations occupying exchangeable cationic sites in the zeolite may be replaced with other cations by ion exchange methods well known to those having ordinary skill in the field of crystalline aluminosilicates. Such methods are generally performed by contacting the zeolite or a base material containing the zeolite with an aqueous solution of the soluble salt of the cation or cations desired to be placed upon the zeolite. After the desired degree of exchange takes place the sieves are removed from the aqueous solution, washed, and dried to a desired water content. By such methods the sodium cations and any non-sodium cations which might be occupying exchangeable sites as impurities in a sodium-X or sodium-Y zeolite can be partially or essentially completely replaced with other cations.

The term "base material" as used herein shall refer to a X or Y zeolite-containing material which can be used to make the special adsorbents described below. Generally the base material will be in the form of particles such as extrudates, aggregates, tablets, pills, macrospheres, or granules produced by grinding any of the above to a desired size range. The adsorbent to be used in our process will preferably have a particle size range of about 16–40 mesh (Standard U.S. Mesh). The X or Y zeolite can be present in the base material in concentrations generally ranging from about 75 wt. % to about 98 wt. % of the base material based on a volatile free composition. The remaining material in the base material generally comprises amorphous silica or alumina or both which is present in intimate mixture with the zeolite material. This amorphous material may be an adjunct of the manufacturing process of the X or Y zeolite (for example, intentionally incomplete purification of the zeolite during its manufacture) or it may be added to the relatively pure zeolite but in either case its purpose is to aid in forming or agglomerating particles of the zeolite. A suitable base material which can be used to make adsorbents for use in this process is "Molecular Sieves 13X" commercially available from the Linde Company, Tonawanda, New York.

We have surprisingly found that certain X zeolites containing specified cations at the exchangeable cationic sites posses the selectivity requirement and other necessary requirements previously discussed and are therefore suitable for use in the process. Some of the suitable X zeolites contain essentially a single cation species at the exchangeable cationic sites while others are essentially completely exchanged with selected cation pairs. A zeolite is deemed to be essentially completely exchanged when the residual sodium content of the zeolite after ion exchange is less than about 2 wt. % Na$_2$O. Specifically we have found that adsorbents comprising a X zeolite containing at exchangeable cationic sites sodium cations or barium cations or strontium cations are all suitable for use in our process. Other adsorbents that can successfully be used are those comprising a X zeolite containing the cation pair barium and potassium or the cation pair barium and strontium at exchangeable cationic sites. An adsorbent containing barium and potassium at the exchangeable cationic sites will preferably have a weight ratio of from about 1:1 to about 100:1 and more preferably within the range of from about 1:1 to about 10:1. An adsorbent containing barium and strontium at the exchangeable cationic sites will preferably have a weight ratio of barium to strontium within the range of from about 1:1 to about 15:1 and more preferably from about 5:1 to about 15:1. We have unexpectedly discovered that many adsorbents predicted to be suitable for use in our process in fact exhibit no selectivity for either a ketose or an aldose and are therefore not suitable for use in the process. Considering, for instance, adsorbents comprising X zeolites containing at exchangeable cationic sites cations of metals of Group IA of the Periodic Table of Elements, we have found that an adsorbent comprising a X zeolite containing sodium cations at the exchangeable cationic sites exhibits selectivity for a ketose with respect to an aldose but an adsorbent consisting essentially of K-exchanged X zeolite does not. Moreover, the latter adsorbent uniquely exhibits reverse selectivity, that is, selectivity for an aldose with respect to a ketose. While an adsorbent comprising sodium-X zeolite exhibits selectivity for a ketose with respect to an aldose and an adsorbent comprising potassium-X zeolite exhibits selectivity for an aldose with respect to a ketose, a cesium-exchanged X zeolite exhibits selectivity for neither a ketose nor an aldose. Considering adsorbents comprising X zeolites containing at exchangeable cation sites cations of metals of Group IIA of the Periodic Table of Elements, an X zeolite essentially completely exchanged with either strontium or barium exhibits selectivity for a ketose with respect to an aldose but an X zeolite essentially completely exchanged with either calcium or magnesium exhibits selectivity for neither a ketose nor an aldose. The reasons why some adsorbents are acceptable for use in our process while others are not is not fully understood at the present time.

The adsorbent may be employed in the form of a dense compact fixed bed which is alternatively contacted with the feed mixture and desorbent materials. In the simplest embodiment of the invention the adsorbent is employed in the form of a single static bed in which case the process is only semi-continuous. In another embodiment a set of two or more static beds may be employed in fixed-bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference thereto. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of our process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zone. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° C. to about 200° C. with about 20° C. to about 100° C. being more preferred and a pressure range of from about atmospheric to about 500 psig. with from about atmospheric to about 250 psig. being more preferred to insure liquid phase. Desorption conditions will include the same range of temperatures and pressures as used for adsorption conditions.

The size of the units which can utilize the process of the invention can vary anywhere from those of pilot-plant scale (see for example our assignee's U.S. Pat. No. 3,706,812) to those of commercial scale and can range in flow rates from as little as a few cc. an hour up to many thousands of gallons per hour.

The following examples are presented to illustrate both the selectivity relationship that makes the process of our invention possible and one embodiment of the separation process and are not intended to unduly restrict the scope and spirit of the claims attached hereto.

EXAMPLE I

This example presents retention volume and selectivity results obtained by pulse tests with ten different adsorbents. Of the ten adsorbents, one comprised an A zeolite, and nine X zeolites. More specifically the A zeolite adsorbent was Linde 5A Molecular Sieves (a calcium-exchanged A zeolite) and the nine X zeolite adsorbents were portions of Linde 13X Molecular Sieves which had been essentially completely ion exchanged with the cations of metals K, Cs, Mg, Ca, Sr, Ba, Ba+K and Ba+Sr. All adsorbents had a particle size range of approximately 20–40 U.S. Mesh.

The general pulse-test apparatus and procedure have been previously described. The adsorbents were tested in a 70 cc coiled column maintained at a process of 55° C. and 50 psig pressure using pure water as the desorbent material. The sequence of operations for each test were as follows. Desorbent material (water) was continuously run through the column containing the adsorbent at a nominal liquid hourly space velocity (LHSV) of about 1.0. At a convenient time desorbent flow was stopped, a 4.7 cc sample of 10 wt. % fructose in water was injected into the column via a sample loop and the desorbent flow was resumed. The emergent sugar was detected by means of a continuous refractometer detector and a peak envelope trace was developed. Another pulse containing 10 wt. % glucose was similarly run. A saturated water solution of benzene was also injected to serve as a tracer from which the void volumn of the adsorbent bed could be determined. Thus for each adsorbent tested three peak traces were developed, one for glucose, one for fructose and one for benzene. The retention volume for glucose is calculated by measuring the distance from time zero or the reference point to the midpoint of the glucose peak and subtracting the distance representing the void volume of the adsorbent obtained by measuring the distance from the same reference point to the mid-point of the benzene peak. For some adsorbents both the fructose and glucose peaks were essentially on top of the benzene peak envelope indicating that both monosaccharides were relatively unadsorbed by the particular adsorbents in the presence of water. The selectivity of an adsorbent for fructose with respect to glucose is the quotient obtained by dividing the fructose retention volumn by the glucose retention volumn. The results for these tests are shown in Table No. 1 below.

TABLE NO. 1

Selectivities of Various Adsorbents for Fructose with Respect to Glucose

| TEST | ADSOR-BENT | RETENTION VOL. OF FRUCTOSE, CC. | RETENTION VOL. OF GLUCOSE, CC. | SELECTIVITY (B) |
|---|---|---|---|---|
| 1 | Na—X | 7.1 | 5.0 | 1.42 |
| 2 | K—X | 11.9 | 21.6 | 0.55 |
| 3 | Cs—X | Both were relatively unadsorbed | | |
| 4 | Mg—X | Both were relatively unadsorbed | | |
| 5 | Ca—X | Both were relatively unadsorbed | | |
| 6 | Ca—A | Both were relatively unadsorbed | | |
| 7 | Sr—X | 8.0 | 1.3 | 6.15 |
| 8 | Ba—X | 27.1 | 9.6 | 2.82 |
| 9 | Ba—K—X | 16.4 | 7.5 | 2.19 |
| 10 | Ba—Sr—X | 21.3 | 4.2 | 5.0 |

The adsorbents used for Tests 1, 2 and 3 were X zeolites each containing a cation from Group IA metals of the Periodic Table of Elements. The Na-X adsorbent used for Test 1, with a selectivity of 1.42, exhibited selectivity for fructose with respect to glucose yet the K-X adsorbent used for Test 2 showed reverse selectivity, that is, selectivity for glucose with respect to fructose while the Cs-X adsorbent used in Test 3 exhibited relative selectivity for neither.

The adsorbents used for Tests 4, 5, 7 and 8 were X zeolites containing at exchangeable cationic sites cations of metals from Group IIA of the Periodic Table of Elements while the adsorbent used for Test 6 was a calcium-exchanged A zeolite. As indicated by the results in Table 1, both fructose and glucose were relatively unadsorbed with the Mg-X, Ca-X and Ca-A adsorbents used in the presence of water for Tests 4, 5 and 6 respectively but both the Sr-X and Ba-X adsorbents used in Tests 7 and 8 respectively exhibited selectively for fructose with respect to glucose. While not wishing to be bound by any theory, we believe adsorbents comprising X zeolites containing at the exchangeable cationic sites a Group IIA cation generally become less acidic as one moves downward from Period 3 to Period 6 of the Periodic Table of Elements in selecting the Group IIA cation. Adsorbents comprising Ca or Mg-exchanged X zeolites are unsuitable for use in our process because they are more acidic while adsorbents comprising a Ba- or Sr-exchanged X zeolite are suitable for use in our process because they are less acidic.

The adsorbents used for Tests 9 and 10 were X zeolites containing at exchangeable cationic sites the cation pairs Ba and K and Ba and Sr respectively. The Ba-K-X adsorbent used in Test 9 exhibited selectivity for fructose with respect to glucose while the K-X adsorbent used in Test 3 did not but the selectivity of the Ba-K-X adsorbent was not as high as the Ba-X adsorbent used in Test 8. The Ba-Sr-X adsorbent used in Test 10 exhibited fructose to glucose selectivity less than the Sr-X adsorbent used in Test 7 but higher than the Ba-X adsorbent used in Test 8.

EXAMPLE II

To assure that fructose could be separated from an actual mixture containing fructose and glucose a solution containing 20 wt. % each of fructose and glucose in water was pulse tested over a 440 cc. bed of adsorbent comprising barium-exchanged X zeolite contained in a ½-in. I.D. by 7½-ft. column. The adsorbent was the same as that used in Test 8 of Example I above and the same operating temperature and pressure as those of Example I were employed. Water as the desorbent material was first passed over the adsorbent then the pulse of feed was injected and then desorbent material flow was resumed. The effluent was analyzed by both refractive index and polarimetry and with this combination quantitative rather than qualitative determinations of the fructose and glucose in the effluent were determined. The larger sample sizes required for these analysis was the reason why a column larger than that used in Example I was used for this example. The results obtained from this example along with those of Test 8 of Example I which used the same adsorbent are shown in Table 2 below.

TABLE 2

Selectivity Comparison with Ba—X Adsorbent

| TEST | RETENTION VOL. OF FRUCTOSE, CC. | RETENTION VOL. OF GLUCOSE, CC. | SELECTIVITY, (B) |
|---|---|---|---|
| Example II | 105. | 35 | 3.0 |
| Test 8 of Example I | 27.1 | 9.6 | 2.82 |

Given the accuracy of the test method, the selectivity obtained when the fructose and glucose were processed together is considered to be the same as that obtained when they were processed separately.

EXAMPLE III

This example illustrates the ability of our process when operated in a preferred embodiment which utilizes a continuous, simulated-moving bed, countercurrent-flow system to separate a ketose from an aldose. Specifically the example presents test results obtained when a synthetic blend of 16.5 wt. % each of fructose and glucose in water was processed using a barium-exchanged X zeolite adsorbent of approximately 20-40 U.S. Mesh particle size range and water as a desorbent material in a pilot-plant-scale testing apparatus, known as a carousel unit, which is described in detail in deRosset et al U.S. Pat. No. 3,706,816 incorporated herein by reference. Briefly the apparatus consists essentially of 24 serially connected adsorbent chambers having about 18.8 cc. volume each. Total chamber volume of the apparatus is approximately 450 cc. The individual adsorbent chambers are serially connected to each other with relatively small-diameter connecting piping and to a rotary type valve with other piping. The valve has inlet and outlet ports which direct the flow of feed and desorbent material to the chambers and extract and raffinate streams from the chambers. By manipulating the rotary valve and maintaining given pressure differentials and flow rates through the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids flow to and from the process. The rotary valve contains a feed input line through which passes a feed mixture containing an extract and a raffinate component, an extract stream outlet line through which passes desorbent material in admixture with an extract component, a desorbent material inlet line through which passes desorbent material and a raffinate stream outlet line through which passes a raffinate component in admixture with desorbent material. Additionally, a flush material inlet line is used to admit flush material for the purpose of flushing feed components from lines which had previously contained feed material and which will subsequently contain a raffinate or extract output stream. The flush material employed is desorbent material which then leaves the apparatus as part of the extract and raffinate output streams. In these carousel-unit tests the raffinate and extract output streams were collected and analyzed for fructose and glucose concentrations by chromatographic analysis but no attempt was made to remove desorbent material from them. Fructose yield was determined by calculating the amount of fructose "lost" to the raffinate stream, determining this quantity as a percentage of the fructose fed to the unit over a known period of time and subtracting this percentage from 100 percent. The operating pressure for the tests was 150 psig. and the operating temperatures were 50° C. and 75° C. respectively for Tests 1 and 2. The fructose purity (as a percent of total sugars present) of the extract output stream and the fructose yield are shown below in Table 3.

TABLE 3

CAROUSEL TEST UNIT RESULTS

| TEST | EXTRACT STREAM FRUCTOSE PURITY, % | FRUCTOSE YIELD, % |
|---|---|---|
| 1 | 80 | 60 |
| 2 | 80 | 71 |

Since the effects of different operating conditions on the product purity and yield relationship have not been completely investigated, the results of Tests 1 and 2 above are not intended to represent the optimums that might be achieved.

We claim as our invention:

1. A process for continuously separating, in liquid phase, fructose from a liquid feed mixture of sugars containing fructose and glucose, fructose being selectively adsorbed by contact with solid adsorbent particles of crystalline aluminosilicate or zeolite, utilizing a simulated countercurrent flow system, wherein liquid streams are allowed to flow through three serially closed loop interconnected zones including a desorption zone, a purification zone and a adsorption zone, each zone being divided into a plurality of serially interconnected beds, each bed being packed with a mass of said solid adsorbent particles, comprising the steps of introducing said liquid feed mixture into the first bed of said adsorption zone, introducing water as a desorbent into the first bed of said desorption zone, withdrawing a portion of a desorption effluent comprising the extract and the desorbent from the bed of said desorption zone for obtaining a product of fructose, withdrawing a portion of a raffinate effluent comprising less adsorbed sugars and the desorbent from a point such that a zone remains between the raffinate outlet stream and the desorbent inlet stream and immediately upstream with respect to the fluid flow to the desorption zone, and all of the points of introducing and withdrawing said liquid streams into and from said beds are simultaneously shifted one bed at a time at predetermined intervals of time, in a downstream direction in the same aliquot portion of the total cycle, and circulating said liquid streams flowing in said three zones without any interruption of flow between said desorption zone and said purification zone.

2. A process for continuous separation of fructose in accordance with claim 1, wherein said solid adsorbent particles are of zeolite in the form of faujasite type X or Y.

3. A process for continuous separation of fructose in accordance with claim 1, wherein the size of said solid adsorbent particles is in the range of from 0.635 to 1.59 mm, the number of said beds is in the range of from 4 to 50, and the interval of time between the shifts is in the range of from 0.5 to 10 minutes.

* * * * *